US009978139B2

(12) United States Patent
Kriheli et al.

(10) Patent No.: US 9,978,139 B2
(45) Date of Patent: May 22, 2018

(54) METHOD AND APPARATUS FOR MONITORING, DOCUMENTING AND ASSISTING WITH THE MANUAL COMPOUNDING OF MEDICATIONS

(71) Applicant: EQUASHIELD MEDICAL LTD., Tefen Industrial Park (IL)

(72) Inventors: Marino Kriheli, Tel Aviv (IL); Eric Shem-Tov, Ramat Hasharon (IL); Gonen Daskal, Kfar Hanasi (IL)

(73) Assignee: EQUASHIELD MEDICAL LTD., Tefen Industrial Park (IL)

( * ) Notice: Subject to any disclaimer, the term of this patent is extended or adjusted under 35 U.S.C. 154(b) by 0 days. days.

(21) Appl. No.: 14/913,808

(22) PCT Filed: Aug. 24, 2014

(86) PCT No.: PCT/IL2014/050755
§ 371 (c)(1),
(2) Date: Feb. 23, 2016

(87) PCT Pub. No.: WO2015/029020
PCT Pub. Date: Mar. 5, 2015

(65) Prior Publication Data
US 2016/0247277 A1   Aug. 25, 2016

(30) Foreign Application Priority Data
Aug. 26, 2013   (IL) .......................................... 228122

(51) Int. Cl.
*G06K 9/00* (2006.01)
*G06T 7/00* (2017.01)
(Continued)

(52) U.S. Cl.
CPC ............ *G06T 7/0012* (2013.01); *B65B 3/003* (2013.01); *B65B 55/02* (2013.01);
(Continued)

(58) Field of Classification Search
CPC ....... B65B 55/02; B65B 55/027; B65B 3/003; G06T 7/62; G06T 2207/30232;
(Continued)

(56) References Cited

U.S. PATENT DOCUMENTS 3,024,701 A * 3/1962 Marks ....................... F21V 3/04
156/242
8,297,320 B2   10/2012 Giribona et al.
(Continued)

FOREIGN PATENT DOCUMENTS

WO   2007/047138 A1   4/2007
WO   2014/152828 A1   9/2014

OTHER PUBLICATIONS

International Search Report for a counterpart foreign application—PCT/IL2014/050755—dated Dec. 16, 2014, three pages.
(Continued)

*Primary Examiner* — Gregory F Cunningham
(74) *Attorney, Agent, or Firm* — Roach Brown McCarthy & Gruber, P.C.; Kevin D. McCarthy

(57) ABSTRACT

The invention is a method and system for monitoring, documenting and assisting with the manual preparation and/or administration of medications. The invention accomplishes these goals via constant surveillance of the preparation/administration process using one or more digital cameras and software and hardware that processes the images and compares data from the processed images with information relative to the patient, to the drug components and composition of the medicament, and to non-drug items needed in the preparation that the system automatically or manually retrieves from various sources, e.g. internal or external data banks, from the technician/pharmacist, or by scanning the prescription.

15 Claims, 5 Drawing Sheets

(51) Int. Cl.
- *B65B 3/00* (2006.01)
- *G07F 17/00* (2006.01)
- *B65B 55/02* (2006.01)
- *G06F 17/30* (2006.01)
- *G06F 19/00* (2018.01)
- *G06K 9/18* (2006.01)
- *G06Q 10/06* (2012.01)
- *G06Q 50/22* (2018.01)
- *G08B 21/18* (2006.01)
- *H04N 7/18* (2006.01)
- *G06T 7/62* (2017.01)

(52) U.S. Cl.
CPC .... *G06F 17/3056* (2013.01); *G06F 17/30247* (2013.01); *G06F 19/3456* (2013.01); *G06K 9/00771* (2013.01); *G06K 9/00973* (2013.01); *G06K 9/18* (2013.01); *G06Q 10/06316* (2013.01); *G06Q 50/22* (2013.01); *G06T 7/62* (2017.01); *G07F 17/0092* (2013.01); *G08B 21/18* (2013.01); *H04N 7/18* (2013.01); *B65B 55/027* (2013.01); *G06T 2207/30232* (2013.01)

(58) Field of Classification Search
CPC ... G06T 7/0012; G07F 17/0092; G08B 21/18; H04N 7/18; G06K 9/18; G06K 9/00973; G06K 9/00771; G06F 19/3456; G06F 17/3056; G06F 17/30247; G06Q 50/22; G06Q 10/06316

USPC .......................................................... 382/128

See application file for complete search history.

(56) References Cited

U.S. PATENT DOCUMENTS

| | | | |
|---|---|---|---|
| 8,777,906 B1* | 7/2014 | Gray | A61M 5/3135 604/181 |
| 9,744,300 B2* | 8/2017 | Kamen | A61M 5/172 |
| 2010/0094653 A1 | 4/2010 | Tribble et al. | |
| 2011/0093279 A1 | 4/2011 | Levine et al. | |
| 2012/0316897 A1 | 12/2012 | Hanina et al. | |
| 2013/0142406 A1* | 6/2013 | Lang | G06K 9/6293 382/128 |
| 2013/0204433 A1 | 8/2013 | Gupta et al. | |

OTHER PUBLICATIONS

Written Opinion of the International Searching Authority for a counterpart foreign application—PCT/IL2014/050755—dated Dec. 16, 2014, five pages.

\* cited by examiner

METHOD AND APPARATUS FOR MONITORING, DOCUMENTING AND ASSISTING WITH THE MANUAL COMPOUNDING OF MEDICATIONS

FIELD OF THE INVENTION

The present invention relates to the field of administering drugs and medications to patients. More particularly, the present invention relates to the field of monitoring, preparation, and the manual compounding of medication.

BACKGROUND OF THE INVENTION

In the preparation and administration of different medications, medical personal are required to make sure that only the correct drugs, accurate dosages, and proper equipment is used. In the simplest case all that is required is that the producer, e.g. a pharmacist or a pharmacy tech, use a syringe to withdraw the required volume of a drug in liquid form from a vial or capsule in which it has been packaged by the manufacturer and then to transfer the syringe to a doctor or nurse to inject the withdrawn volume of drug directly into a vein of the patient or into an infusion bag. In a more complex procedure the drug may come in powdered form contained within a vial and must be reconstituted by injecting a suitable diluent, e.g. distilled and/or deionized water or saline solution into the vial with a syringe, thoroughly mixed, and then the required dosage withdrawn using the same in a different syringe.

In hospital settings each patient may receive medication in many forms, e.g. pills, injections, and IV drips. Each patient receives his own individual prescription according to a schedule determined by his doctor. Depending on the hospital's procedures, a pharmacist or a pharmacy-technician is responsible for preparing the prescribed medication, including compounding medications by combining and/or processing appropriate ingredient(s) utilizing various pieces of medical equipment, properly labeling the medication for each patient, and providing it to a nurse for administration.

Amongst the more complex and potentially dangerous procedures carried out in hospital pharmacies is the compounding of "cocktails" for treatment of diseases such as AIDS and cancer. Because of the hazardous nature of the drugs that make up the cocktail, the complexity of their preparation, the accurate dosage required, the frequency by with they are administered to the patient, and the physical condition of the patient, a great deal of skill and attention to detail is required in their preparation. Chemotherapeutic agents are usually prescribed by a medical oncologist or a hematologist. A chemotherapy regimen (schedule) typically consists of a specific number of cycles given over a set period of time. A patient may receive one drug at a time or combinations of different drugs at the same time. After the chemotherapeutic agent is prepared for the patient, the patient receives the medication, which can be administered intravenously, orally, as an injection to the fatty part of the arm, leg, or abdomen, intra arterially, intraperitoneally, or topically.

Obviously the consequences to the patient, of errors in compounding the drugs, can be very severe; however, also contact with the drugs or their vapors can be potentially very hazardous to the personal that prepare the medicaments and administer them as well. Therefore proper protocols must also be followed "to the letter" to avoid errors and accidents.

To prevent, or at least to minimize, the number of mistakes many methods and systems, including computerized systems, which monitor the work of the pharmacist/pharmacy-technician, and alert when a mistake occurs, have been devised.

An example of a prior art system with an automated machine for preparation of pharmaceutical products is disclosed in U.S. Pat. No. 8,297,320. This patent describes an apparatus contained within a box-type holding frame, which defines a chamber. The apparatus is comprised of a gripping and carrier mechanism to transfer a container between a magazine containing a plurality of containers, e.g. syringes, and a dosage station comprising a flat turntable, adapted to receive and hold three syringes having different diameters and lengths, where the pharmaceutical product is prepared. The chamber has an access aperture to the magazine. A pneumatic device, with a fan wheel to assure air circulation, is adapted to supply a sterile air flow through the entire chamber and to prevent the exchange of air with the outside environment.

It is a purpose of the present invention to provide a complete system for guiding, monitoring, and documenting the process of preparation of medication for administration to patients.

Further purposes and advantages of this invention will appear as the description proceeds.

SUMMARY OF THE INVENTION

In a first aspect the invention is a method for monitoring, documenting and assisting with the manual preparation and/or administration of medications. The method comprises the steps of:
  a) using at least one digital camera to provide constant surveillance of the preparation/administration process;
  b) providing software adapted to perform image processing of images acquired by the at least one digital camera and to compare, in real time, data extracted from the processed images to one or more of information relative to a patient, drug components and composition of the medication, and non-drug items needed in the preparation, wherein the data is automatically or manually retrieved from various sources; and
  c) providing dedicated software algorithms that are adapted to act as an interactive assistant guiding and/or supervising a producer through each step of a specific preparation process Embodiments of the method of the invention comprise providing software adapted to compile complete documentation of the medication preparation process in the form of visual and data archives of the preparation steps, in which every step in the preparation process is documented and indexed.

Embodiments of the method of the invention comprise a stage comprised of general steps that are followed for filling any type of prescription. In this stage the algorithms in the software are adapted to verify the correct match of a prescription to a patient and to his/her medical condition and to supervise or guide a producer when selecting the prescribed drugs and equipment needed for the preparation process.

Embodiments of the method of the invention comprise a visual or aural warning to alert the producer if an error is detected at any stage of the preparation or administration process.

In embodiments of the method of the invention the images and data that are processed by the software are saved together with the parameters that the software has deduced for the objects visible in the images.

In embodiments of the method of the invention barcode recognition, QR code recognition, OCR (Optical Character Recognition), and additional pattern recognition algorithms are used to supply data from the images.

In embodiments of the method of the invention images of a syringe are analyzed to determine at least one of the following:
   a) the type and size of the syringe;
   b) whether the syringe is filled with air or transparent liquid;
   c) whether bubbles are present in the liquid in the syringe;
   d) to determine the volume of the bubbles; and
   e) to measure the volume of liquid in the syringe by recognizing the piston of the syringe and a reference line on the barrel of the syringe and measuring the distance between them.

In a second aspect the invention is a system for monitoring, documenting and assisting with the manual preparation and/or administration of medications. The system comprises:
   a) at least one digital camera adapted to provide constant surveillance of the preparation/administration process;
   b) a processor unit comprising:
      i) software adapted to perform image processing of images acquired by the at least one digital camera and to compare, in real time, data extracted from the processed images to information relative to one or more of a patient, drug components and the composition of the medication, and non-drug items needed in the preparation, wherein the data is automatically or manually retrieved from various sources;
      ii) dedicated software algorithms that are adapted to act as an interactive assistant guiding and/or supervising a producer through each step of a specific preparation process; and
   c) a display screen adapted to serve as an interface between the producer and the software of the system.

In embodiments of the system of the invention the processor unit additionally comprises software adapted to compile complete documentation of the medication preparation process in the form of visual and data archives of the preparation steps, in which every step in the preparation process is documented and indexed.

Embodiments of the system of the invention are adapted to produce a visual or aural warning to alert the producer if an error is detected at any stage of the preparation or administration process.

In embodiments of the system of the invention the image processing software is adapted to use barcode recognition, QR code recognition, OCR (Optical Character Recognition), and additional pattern recognition algorithms to supply data from the images.

In embodiments of the system of the invention the image processing software is adapted to process images of a syringe taken by the at least one digital camera in order to determine at least one of the following:
   a) the type and size of the syringe;
   b) whether the syringe is filled with air or transparent liquid;
   c) whether bubbles are present in the liquid in the syringe;
   d) to determine the volume of the hubbies; and
   e) to measure the volume of liquid in the syringe by recognizing the piston of the syringe and a reference line on the barrel of the syringe and measuring the distance between them.

Embodiments of the system of the invention comprise an illuminated surface on which a syringe can be placed. In these embodiments of the system of the invention the source of illumination can be polarized.

Embodiments of the system of the invention are adapted to be portable.

All the above and other characteristics and advantages of the invention will be further understood through the following illustrative and non-limitative description of embodiments thereof, with reference to the appended drawings.

DETAILED DESCRIPTION OF EMBODIMENTS OF THE INVENTION

Figure 1:
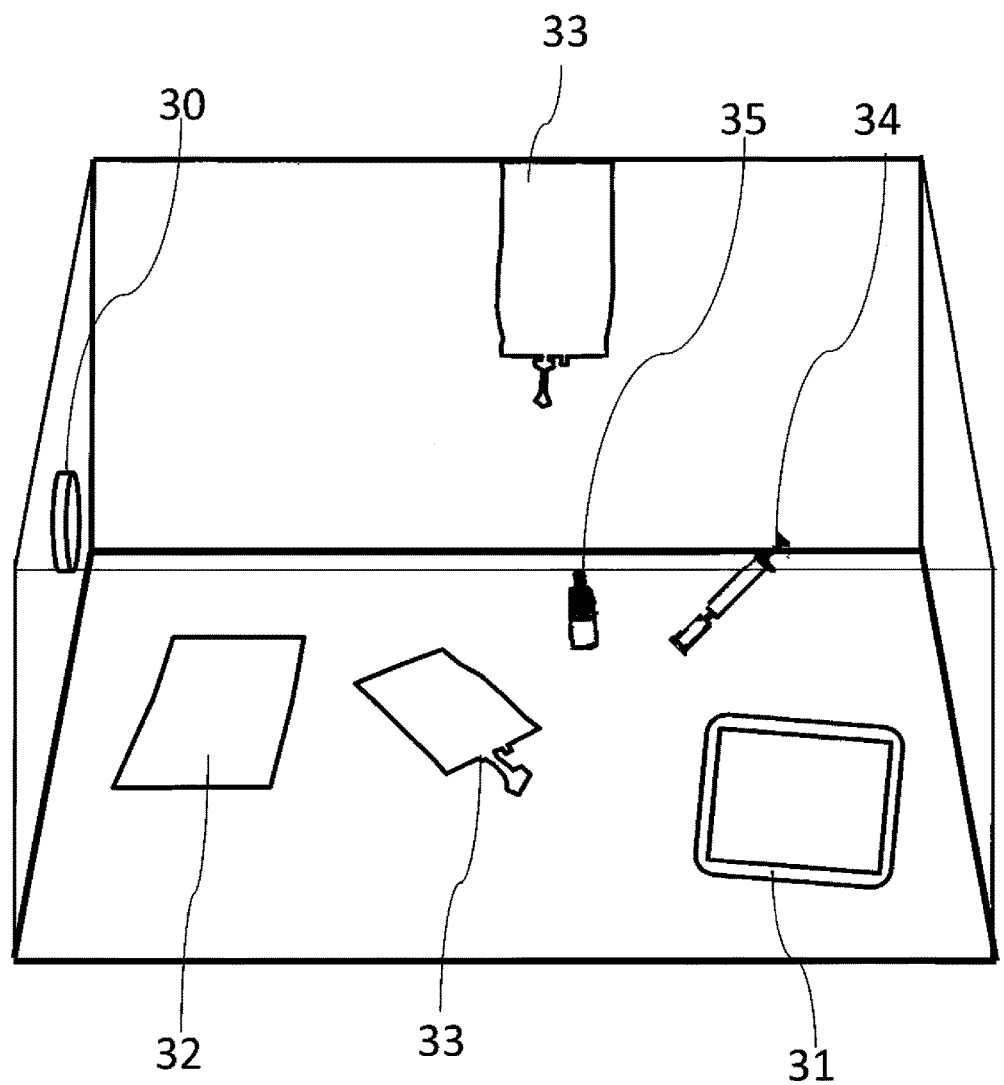
FIG. 1 schematically illustrates an example for a workspace for compounding medications.

The invention is a method and system for monitoring, documenting and assisting with the manual preparation and/or administration of medications. The invention accomplishes these goals via constant surveillance of the preparation/administration process using one or more digital cameras and software and hardware that processes the images and compares data from the processed images with information relative to the patient, to the drug components and composition of the medicament, and to non-drug items needed in the preparation that the system automatically or manually retrieves from various sources, e.g. internal or external data banks, from the technician/pharmacist, or by scanning the prescription.

The invention is based on image processing, and the monitoring of the preparation process is done using image processing technology. Complete documentation of the medication preparation process is based on a visual archive of the preparation steps, in which every step in the preparation process is documented and indexed in various ways, e.g. by the patient's or pharmacist's or doctor's identity or by date, and initially stored in a local memory unit that is a part of the processor of the system. For example, the documentation is stored in the pharmacy until the patient is released from the hospital and then sent by wireless or wired technology to be archived in a remote data memory unit. The saved data/documentation can comprise such information as: time stamps; details of prescriptions; patient identification and information, e.g. sex, age, weight, height, disease being treated; preparation phase details, e.g. comments, confirmations, alerts; log messages, e.g. errors, warnings, trace, debug; identification and verification of supervisor's permission if required; details of the technician that prepared the prescription and the supervisor; a visual archive of images taken during the preparation phase; and information regarding the dispensing phase.

The system of the invention comprises an internal database that is updated manually, according to the hospital guidelines, by an administrator and/or automatically from the hospital's databases. In embodiments of the invention the system can be connected to external databases of other hospitals, health institutes (e.g. FDA=Food and Drug Administration and NIH=National Institute of Health) and manufacturers, via a communication network.

Typical of the wide variety of information that can be included in the database and used by the algorithms in the software of the invention is:

a) Packaging dosage, physical properties, reconstitution, dilution dosages and dispensing instructions etc. of drugs. The information can be continuously updated, either automatically or manually, with information from sources such as the FDA, NIH and medicines companies.

b) Capacity, catalog numbers, National Drug Code (NDC) numbers, barcodes, or other identifying features of IV Bags. The information is continuously updated, either automatically or manually, with information from the FDA, NIH and producer companies.

c) Capacity, catalog numbers, dimensions or other identifying features of syringes and adaptors. The information is continuously updated, either automatically or manually, from sources such as catalogues of medical products manufactures and distributers.

d) Images and video streams, both raw and processed taken by the system camera/s.

In one embodiment of the system, the system automatically compares dosages and diluents on the prescription to data in the drug manuals, or other data inserted into the system's database and verifies that the prescribed doses comply with the recommended dose tolerances in order to avoid errors and resulting wrong dosages. In case of differences between the prescribed and recommended doses the system sends an alert via the interface to the producer, i.e. the pharmacist, pharmacist technician or other person using the system of the invention, and optionally to the prescribing doctor or other hospital personnel.

In one embodiment, the invention is a workflow driven system with a software automation tool based on a physician defined prescription that acts as an interactive assistant guiding the producer (pharmacist or pharmacist tech) through the production process. The system of the invention is designed to guide, monitor and document every step of the manual preparation, including compounding, of the medication. In case an error is detected, a visual or aural warning is produced by the system to alert the producer. All steps of the preparation process are recorded and stored in memory for later reference.

FIG. 1 schematically illustrates a work-space for filling prescriptions or compounding medications according to the invention. The hardware components of the system of the invention that are shown in FIG. 1 include: one or more digital cameras (30) which are located above the work-space table, next to the table or attached to the body of the producer and have a field of view large enough to cover the areas of interest; a display screen (31) serving as the interface between the producer and the system; and the work surface (32) itself. The screen can be part of a processor, i.e. a single unit, or communicate with it by means of wired or wireless technology (not shown). The processor could be, for example, a PC or mobile device such as a cellular phone or notepad. The processor comprises dedicated software for processing and interpreting images received from the camera or cameras 30; communication means for connecting to external databases and memory units for storing images and data collected during the process of filling the prescription, e.g. via the internet or the hospital's local area network; optional internal databases and memory units for temporary or permanent storage of at least some of the data used and collected; and dedicated software comprising algorithms adapted to guide and supervise the producer. In embodiments of the system of the invention the system may further comprise other equipment, e.g. a label printer, a label dispenser, and/or a sterilizer unit (not shown). Also shown in FIG. 1 are examples of some of the items typically involved in the compounding of medicaments. These items include: an IV bag (33), a syringe (34), and a drug vial (35).

Embodiments of the invention employ two types of camera:

1) High resolution cameras are used for the supervision of the drug dispensing process. These cameras can be either still or video cameras. The still cameras can be triggered by several different means, e.g. foot pedal, voice command, pressing an icon on the display screen, light change, distance from a vicinity sensor. The video cameras will send images to the vision processing algorithm. When the algorithm recognizes an interpretable image it will process it and send feedback to the operator of the system.

2) Wide field of view video cameras that cover the entire working area. The files from this camera will be used for documentation only.

There are two methods in which the system can be implemented. In the first method, which is a "Free Style" method, the video cameras cover the entire working area and the technician works freely, independently of the operation of the camera. In this method the entire video sequence and/or only selected frames that show specific stages in the preparation procedure will be stored in a database for future documentation. In the second method the producer should place the equipment, e.g. a vial, syringe, or bag, at a specific location in the field of view of the still or video cameras, which are then activated by the producer or by the software to capture and process an image.

The images that are processed by the software will be saved with the parameters that the software deduced for the objects visible in the images, i.e. syringe volume, NDC numbers, drug name etc. The identification of the items employed in the medication preparation process is carried out automatically by the algorithms of the software in the processor, which compares the processed images with information drawn from the databases. The software is adapted to use barcode recognition, QR code (Quick Response Code), OCR (Optical Character Recognition), and additional pattern recognition algorithms to deduce and interpret the following data from the images:

1) Syringe:
   a. Syringe size (e.g. 20 cc, 30 cc, 60 cc) by recognizing code or writing on the label, or by measuring the syringe and comparing the measurements to values in the system's database.
   b. Syringe brand by recognizing code or writing on the label, or by measuring the syringe and comparing the measurements to values in the system's database.
   c. Volume of drug in the syringe by recognizing the position of the piston compared to the graduation marks on the syringe or by measuring the distance between the syringe piston and a mark on the barrel or the end of the syringe barrel, and calculating the volume from the geometry of the syringe or by interpolation according to data in the systems database.
   d. Syringe ID. In an embodiment of the system, the syringe is labeled for use in the system. Each syringe is given an ID, e.g. barcode, other characters, or color. This label will be recognized in images of the syringe and read by the software using OCR or other means.
   e. The existence of a bubble in the liquid in the syringe and an estimation of its size by pattern recognition.

2) Drug and Bottle (vial);
   a. Vial size by geometry interpretation and label reading.
   b. Drug information, e.g.: type (generic name); volume; state (powder or liquid); concentration; special characteristics, e.g. sensitivity to light and need to filter; recommended dose; and recommended diluents. The information is obtained by using OCR to recognize the NDC or commercial name on the bottle and comparing the information with system's database.
   c. Drug expiration date and lot number by OCR from a label on the drug container.
   d. Manufacturer's #LOT number by means of OCR
3) Infusion bag: bag material, liquid type, volume, expiration date, lot number, by reading a barcode or QR code recognition and/or NDC number by OCR.
4) Details of the prescription as it appears on a sticker that is either attached to an infusion bag or other object or is scanned alone before being attached to an object, e.g. a syringe, by means of character recognition (OCR) of the printing on the sticker.

The use of digital cameras gives the system of the invention flexibility to interpret patterns, characters, barcode, and QR code using just one type of sensor (i.e. the camera). This is in contrast to, for example, laser scanners that might recognize barcodes and the outlines of an object, but not characters or patterns that might appear within an object, for example the position of the syringe piston within the syringe barrel.

The current state of the art for drug preparation control is based on the use of a weighing scale. This method allows a very accurate control of the weight of the drug and infusion liquids, which can be directly converted into volumes; but it doesn't allow the evaluation of any information that is not weighable like: drug type, infusion liquid type, lot numbers, expiry dates and bubble recognition. Another advantage of the use of camera compared with the weighing method is the flexibility and the ease of the use of the system. At no stage, does the producer need to stop his flow of work, or place the objects on a scale without touching them, and to wait for the scale to stabilize before taking a reading. All that the producer needs to do is to present the object, e.g. drug vial, syringe, label, IV bag, to the camera at specific times.

The algorithms in the software of the processor of the system of the invention may be adapted to act as an interactive assistant guiding the producer through the preparation process. This process includes choosing the correct drugs and equipment for the preparation according to the prescription and, optionally, verifying the correct match of the prescription to the patient by comparing the prescription to the patient's medical history.

The method of the invention can be carried out in many different ways, representative examples of which are described in the following examples. It is to be understood that many other scenarios are possible and that some of the steps may be eliminated, others added, and the order of the steps may be changed depending on the exact nature of the prescription to be filled and/or the drugs to be compounded.

Figure 2:
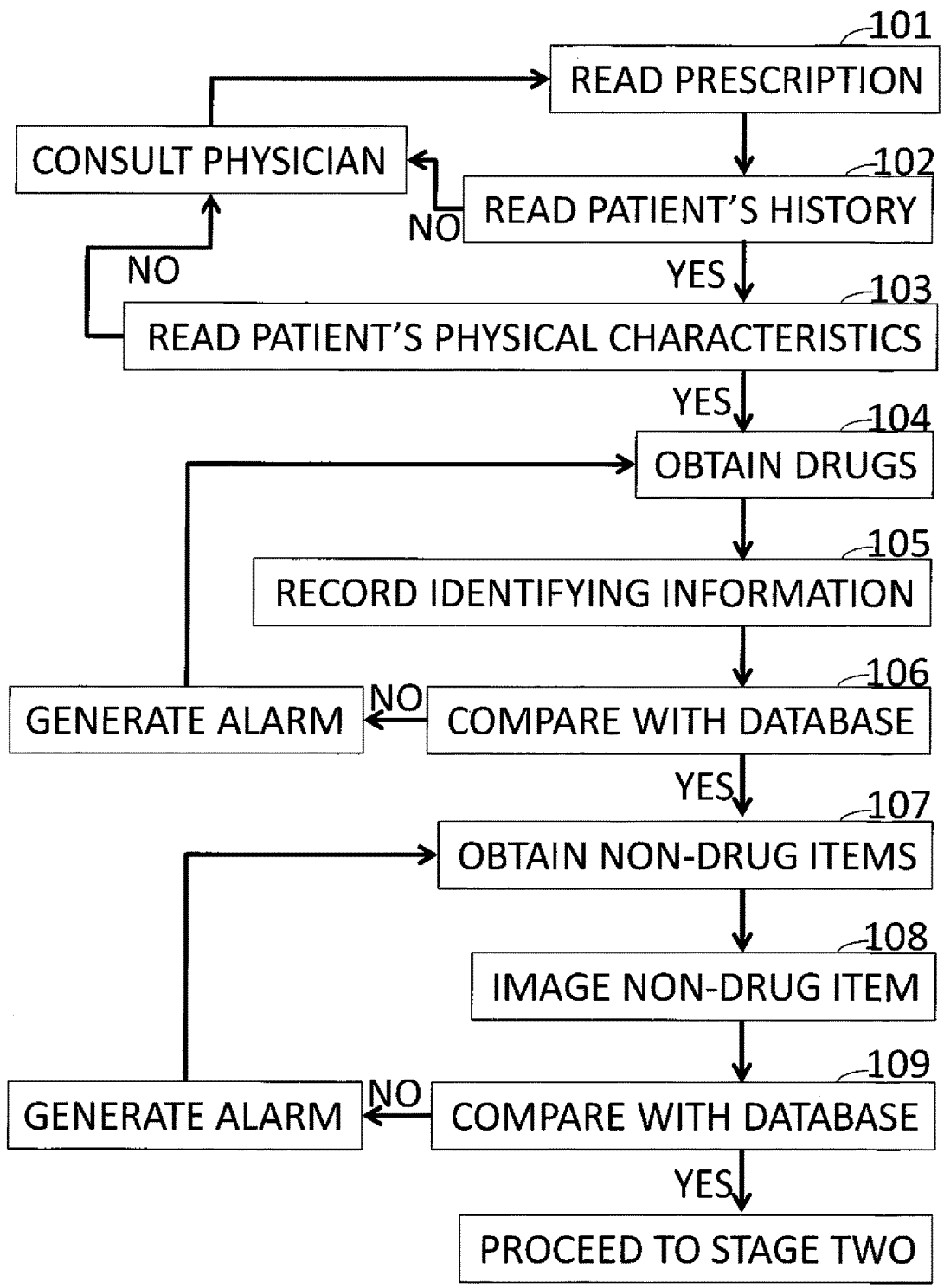
FIG. 2 is a flow chart that schematically shows the steps in the first stage of the process of the invention.

An embodiment of the method of the invention is comprised of two stages. The first stage, which is illustrated in FIG. 2, comprises general steps that are followed for filling any type of prescription. In this stage the algorithms in the software of the invention are adapted to verify the correct match of the prescription to the patient and his/her medical condition and to supervise or guide the producer when selecting the correct drugs and equipment for the preparation. In the second stage the algorithms in the software of the system of the invention are adapted to act as an interactive assistant guiding and supervising the producer through the preparation process. The exact steps of the second stage of the process are very specific to the prescription being filled. Some typical examples will be described in FIGS. 3, 4A, and 4B.

FIG. 2 is a flow chart that schematically shows the steps in the first stage of the process of the invention. The process shown is only meant to illustrate the capabilities of the system of the invention. In practice the first stage can be carried out exactly as described or in many different variations in which the order in which the steps are carried out is changed and/or some of the steps are not carried out at all.

This stage of the process is initiated (101) when an image of a label containing the prescription to be filled is taken by one of the cameras of the system and the information on the label is read using the OCR software in the system processor. The label is made out according to the instructions of the physician and, in addition to personal identifying information of the patient, comprises all information needed by the producer in order to prepare the drug for administration to the patient. The prescription label is typically attached to the means, e.g. IV bag or syringe, with which the prepared drug is to be administered to the patient. Examples of the information on the prescription label are the generic and brand names of the drug to be administered, method of administration, e.g. IV drip or injection, type of diluent, and calculated dilution rate. The prescription read from the image is compared with that in the hospital data network in order to insure that the producer will be working on the correct prescription and also to be certain that the UCH software has accurately read the writing on the label.

In an embodiment of the invention, the system is adapted to manage the preparation flow in the pharmacy and to divide the different preparations between more than one producer. This option is useful because in most hospital pharmacies there is a constant flow of prescriptions that need to be prepared coming from the hospital's data network. Some of these prescriptions will be urgent while others might need to be canceled or delayed (for example, because the patient's condition suddenly deteriorates while waiting for the treatment).

In embodiments of the system of the invention, a display screen is located outside the preparation room, for example in the pharmacy office, or in a hospital administrator's or manager's office. This screen can be a split screen that will show videos from every cabinet in which the system is installed or can display the actual screen images from the GUI of each of the producers that are working with the system at any given time.

In step 101 the system also verifies that the correct IV bag or syringe for administration of the drug to the patient has been selected. In this step the system also verifies drug exceptions, i.e. if the drug requires handling with non PVC equipment, light or sunlight protection, etc. In step 102, the algorithm in the system processor reads the patient's medical history from the hospital data base and consults its internal data base, which is constantly updated with the latest information from external data bases, e.g. those of the hospital, national ministry of health, drug and medical equipment manufacturers, the FDA or NIH, to determine if the prescribed drug or combination of drugs is suitable for the patient's condition. If the answer is 'no' then the system either prompts the producer to contact the prescribing physician or does so directly, e.g. by email or SMS, to verify his instructions. If the answer is 'yes', then the process proceeds to step 103. In this step the system, via the display screen 31 prompts the producer to obtain containers containing drugs having the prescribed active ingredients and diluents from the pharmacy storage units. The producer obtains the recommended drug containers and places them on the working surface 32. In step 105, images of the drug containers are recorded by the system and the image processing software generates identifying data, e.g. from the printing on the label, bar code, color of the contents, NDC number, etc. that is compared in step 106 with similar data in the internal database of the system and the prescription just read, to verify that the correct drug and volume of drug in the container has been placed on the work surface. If, in step 106, an error is detected, then an audible or visual (or both) alarm is generated by the system. In this step as in all other image gathering steps of the procedure, if the system is unable to image sufficient identifying data, it may prompt the producer to move or rotate the drug container. If moving or rotating the drug container doesn't remove the source of the error, then the process returns to step 104, or the system can allow the producer, or his supervisor, to insert the data manually. For that purpose special authorization will be needed, e.g. a password or a magnetic card. If no error is detected, then the process proceeds to step 107 in which the producer is prompted to select the non-drug items that are needed to prepare the medication called for in the prescription, e.g. syringes of a certain size and container with the required diluent if a reconstitution process is required. In step 108, images of the items on the workplace are recorded by the system and, in step 109, the image processing software compares identifying features of the items, e.g. manufactures catalogue numbers, volume scales printed on the item, with similar features from a the internal database of the system and determines whether the correct items have been selected when compared to the prescription. If in step 109 an error is detected then an audible or visual alarm (or both) is generated by the system and the process returns to step 107. If no error is detected, then the process proceeds to stage 2.

It is again emphasized that FIG. 2 shows many steps that are optional and that in different embodiments the algorithms in software of the processor of the system of the invention can be configured to function with or without these features. For example, in some embodiments steps 102 and 103 are not executed and the algorithms assume that the prescription, as written by the physician and read in step 101, is correct. As another example, in step 107 the system may not be adapted to determine which non-drug components are necessary to prepare the medication. The producer may choose the components on the basis of his knowledge and experience or with reference to professional literature or specialized databases.

It is noted that the second stage, examples of which will be described herein below, can be carried out independently of the first stage and in some embodiments of the method the first stage is not carried out at all.

Figure 3:
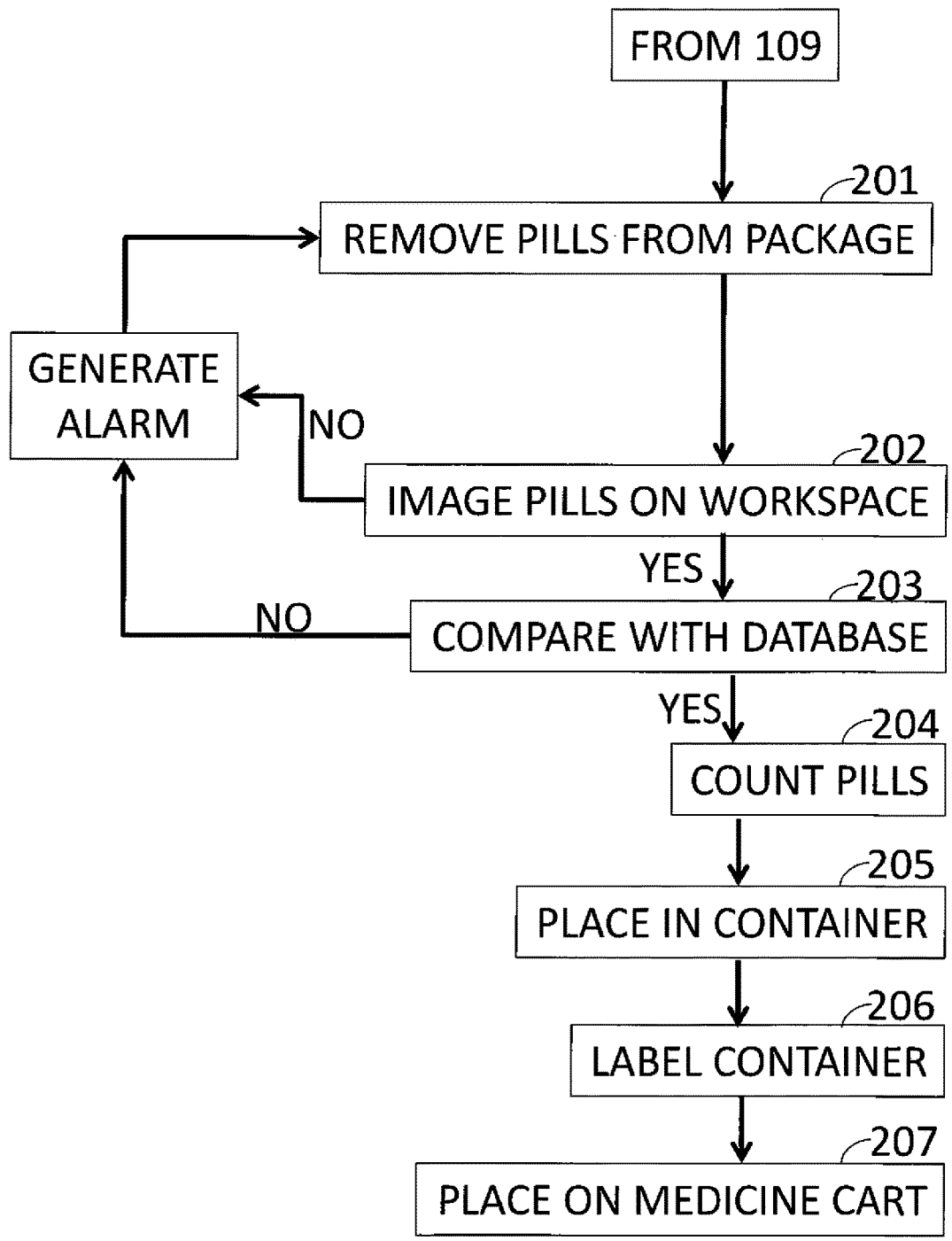
FIG. 3 is a flow chart that schematically illustrates the second stage of a simple process of filling a prescription.

FIG. 3 is a flow chart that schematically illustrates stage 2 of a simple process of filling a prescription, which calls for the administration of two pills to lower the blood pressure and an anti-depressant capsule to a patient. Despite the apparent simplicity of the procedure, all steps of the first stage are followed. These drugs are normally supplied in packaging, e.g. bottles, containing relatively large quantities of the drug, therefore, in step 201 the producers removes the required number of pills from each package and lays them on the work surface. In step 202 images of the work surface are scanned and the image processing software identifies characteristics of the pills such as color, shape, and identifying marks. In step 203 the features identified from the scans are compared with information from a database, such as that of the drug manufacturer. This step is carried out to confirm that the containers have not been mislabeled or that pills have not been inadvertently returned to the wrong bottle in an earlier preparation procedure. If the system cannot verify that the correct pills have been selected, an alarm is generated and the process returns to step 201. If the system verifies that the correct pills have been selected the process continues to step 204. In step 204 the software analyzes the images to determine if the correct number of pills of each type has been removed from the containers. If the answer is 'no', the process is returned to step 201. If the answer is 'yes', then the pills are placed in a container, e.g. a paper cup, that has been placed on the work surface in step 107 of the first stage. In step 206 a label on which is written information, such as the ward and room number of the patient, his name and identity number, and other information such as the date and time the medication was prepared and by whom, when the medication is to be administered, the prescribing physician, etc. is created and placed on the container containing the pills. It is noted that step 206 can be carried out as shown or earlier, for example after step 109 or after step 204. Finally, in step 207, the labeled container is placed on a drug cart to be delivered to the staff member responsible for administering it to the patient.

Figure 4A:
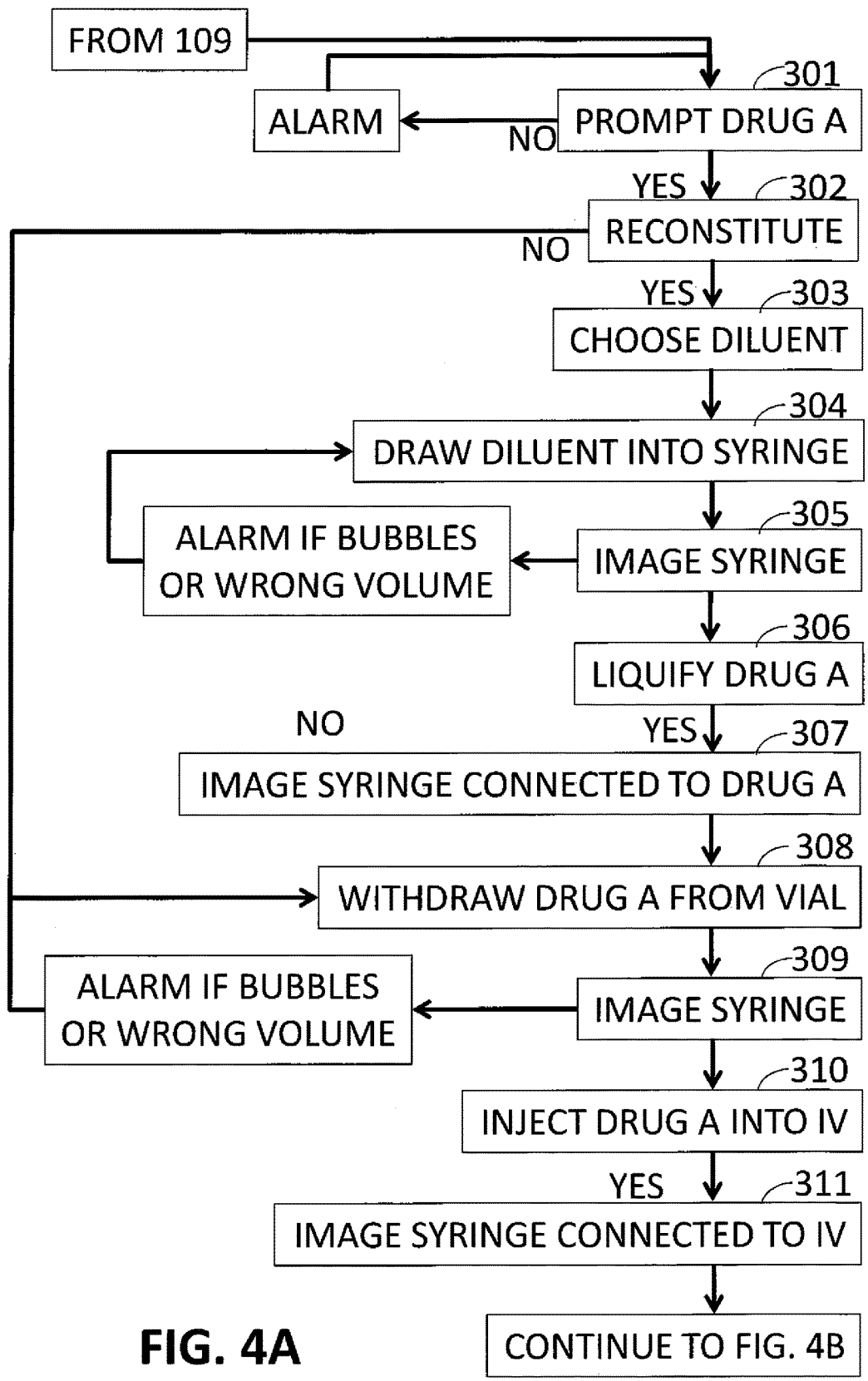
FIG. 4A and FIG. 4B are two parts of a flow chart that schematically illustrates the second stage of a much more complex compounding procedure.
Figure 4B:
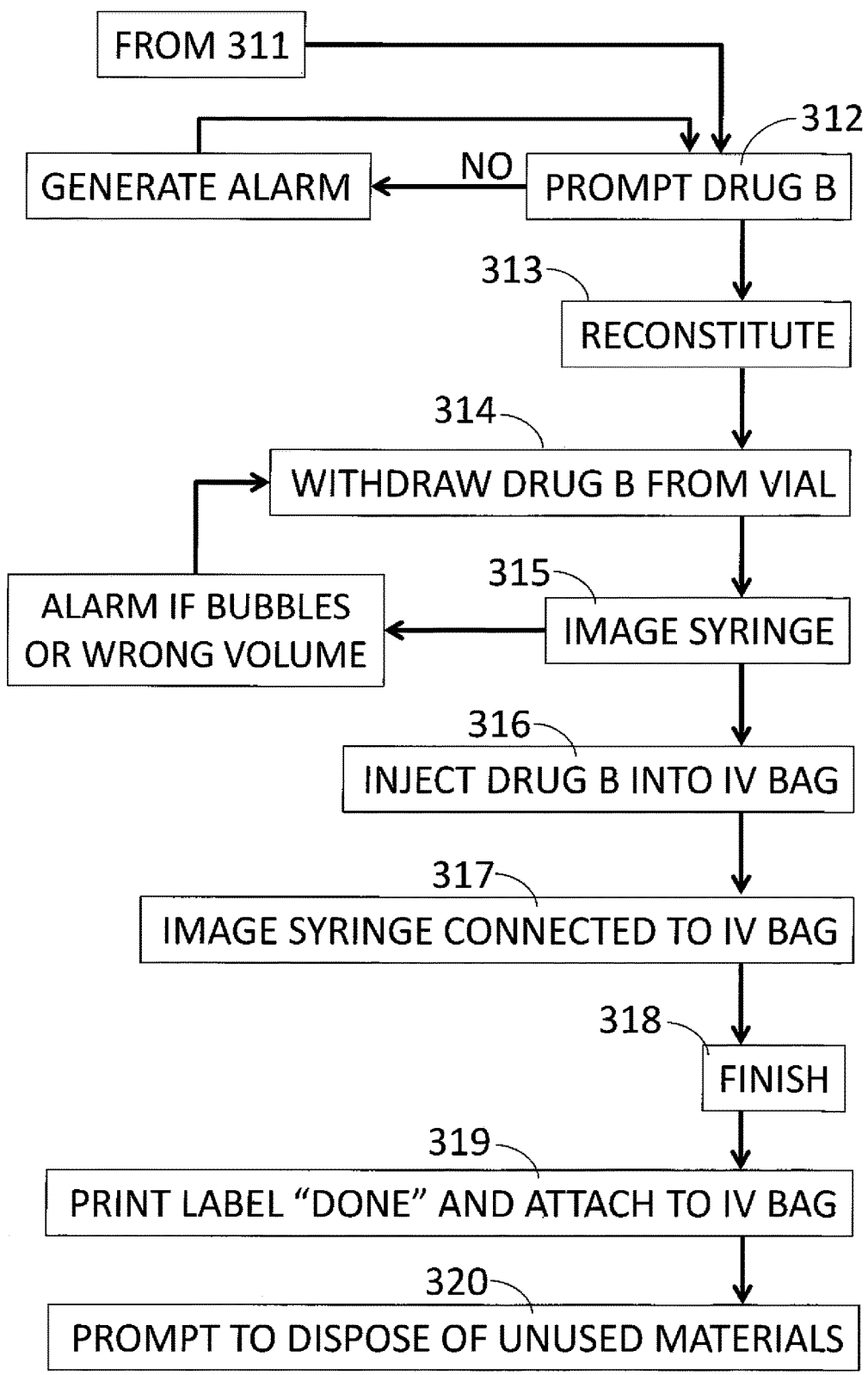

FIG. 4A and FIG. 4B are two parts of a flow chart that schematically illustrates stage two of a much more complex compounding procedure. In this example the prescription calls for administering a medication comprised of two drugs to a patient by means of an IV drip. Drug A is supplied as 2 grams of dry powder in a 20 ml glass vial and drug B is supplied as a liquid in a 20 ml glass vial. The prescription calls for 1 gram of reconstituted drug A and 10 ml of drug B added to an infusion bag to which the prescription label (see step 101) is attached.

In step 301, the producer is prompted to place drug A in the field of view of one of the cameras of the system, which images the vial containing drug A. The software in the processor analyzes the images to determine if the drug matches that called for in the prescription. If the answer is no, an alarm is generated and the producer must locate the correct drug bottle. If the answer is yes, then the process proceeds to step 302.

In step 302 images of the drug bottle are analyzed and the NDC number or a barcode are read to determine if the drug has to be reconstituted. Since the drug contained in the bottle may have been previously reconstituted, e.g. is "left-over" from a previous preparation, the system prompts the producer asking him to verify, e.g. by pressing an icon on a display screen, that a reconstitution process has to be carried out. If the answer is no, then the process skips ahead to step 308. If the answer is yes, then the process continues to step 303.

In step 303 the system instructs the producer to select a particular diluent. The container, e.g. an IV bag that contains the diluent, is imaged by the system camera and the algorithm in the software reads information on the container and compares the result with the database to determine if the correct diluent has been selected. If the answer is no, an alarm is generated and the system prompts the producer to select a different diluent. If the correct diluent has been selected, then the process proceeds to step 304.

In step 304, the system prompts the producer to fill a certain sized syringe with a specified volume of diluent. In step 305, the syringe is separated from the container with diluent and images of the filled syringe are analyzed. The software algorithms of the system search for bubbles in the liquid in the syringe and also measure the volume and compare it with the volume that is recommended in the system database. If bubbles are detected and/or the volume of diluent is incorrect, then an alarm is generated and the producer follows the known procedure to eliminate them and the process returns to step 304 to adjust the volume of diluent in the syringe. If there are no bubbles and the volume is correct then the process proceeds to step 306.

In step 306, the system prompts the producer to connect the syringe containing the diluent to the vial containing drug A and to inject the diluent into the vial. In step 307, the syringe is imaged while still connected to the vial and the images are analyzed to confirm that the syringe is now empty, i.e. to confirm that the required volume of diluent has been added to powdered drug A inside the vial. In step 308, after thoroughly mixing the contents of the vial, the producer is prompted to draw the required volume of reconstituted drug A from the vial into a syringe.

In step 309, the syringe is separated from the vial containing reconstituted drug A and images of the filled syringe are analyzed. The software algorithms of the system search for bubbles in the liquid in the syringe and also measure the volume and compare it with the volume that is called for in the prescription. If bubbles are detected and/or the volume of drug A is incorrect, then an alarm is generated and the producer follows the known procedure to eliminate the bubbles and the process returns to step 308 to adjust the volume of drug A in the syringe. If there are no bubbles and the volume is correct then the process proceeds to step 310.

In step 310, the system prompts the producer to connect the syringe containing reconstituted drug A to the IV bag that will be administered to the patient and to inject drug A into the IV bag. In step 311, the syringe is imaged while still connected to the IV bag and the images are analyzed to confirm that the syringe is now empty, i.e. to confirm that the required volume of drug A has been added to the IV bag.

Preparation with drug A has now been completed. In step 312, the producer is prompted to place drug B in the field of view of one of the cameras of the system, which images the vial containing drug B. The software in the processor analyzes the images to determine if the drug matches that called for in the prescription. If the answer is no, an alarm is generated and the producer must locate the correct drug bottle. If the answer is yes, then the process proceeds to step 313.

In step 313 images of the drug bottle are analyzed and the NDC number or a barcode are read to determine if the drug has to be reconstituted. Since drug B does not have to be reconstituted, the process proceeds to step 314.

In step 314, the producer is prompted to draw the required volume of drug B from the vial into a syringe.

In step 315, the syringe is separated from the vial containing drug B and images of the filled syringe are analyzed. The software algorithms of the system search for bubbles in the liquid in the syringe and also measure the volume and compare it with the volume that is called for in the prescription. It bubbles are detected and/or the volume of drug B is incorrect, then an alarm is generated and the producer follows the known procedure to eliminate the bubbles and the process returns to step 314 to adjust the volume of drug B in the syringe. If there are no bubbles and the volume is correct then the process proceeds to step 316.

In step 316, the system prompts the producer to connect the syringe containing drug B to the IV bag that will be administered to the patient and to inject drug B into the IV bag. In step 317, the syringe is imaged while still connected to the IV bag and the images are analyzed to confirm that the syringe is now empty, i.e. to confirm that the required volume of drug B has been added to the IV bag.

Preparation with both drugs A and B has now been completed (step 318). In step 319 a label with the word "DONE" or a similar word or other data, printed on it is produced and affixed to the IV bag containing drugs A and B. All relevant information including the patient's name and contents of the IV bag are already present on the prescription label that was attached to the bag in step 101.

Finally, in step 320, the producer is prompted how to dispose of the unused materials, e.g. he is told if the volume of drug B or reconstituted drug A remaining in the respective vials can be returned to the storage unit and if so under what conditions, e.g. refrigerated or at room temperature.

In all of the procedures for filling prescriptions, especially when dealing with toxic drugs and those which are easily detrimentally affected by contamination, the system, via the display informs the producer of the correct procedures to maintain sterility and safety.

In addition to being set up in hospital pharmacies as described herein above, portable embodiments of the system can be provided, for example on the carts used to dispense medication to patients in the hospital wards. With the exception of the work surface, the rest of the system can be provided as a hand-held unit comprising a still or video camera, a display screen, and processing unit. The hand-held system can be embodied either as a dedicated unit or as an application to a cellular phone. In this embodiment the camera can be used to verify the identity of the patient by imaging the medical chart attached to his/her bed or the patient's wrist band.

Embodiments of the invention can comprise facial recognition software to accomplish this step. Once the identity of the patient has been confirmed, the person administering the medication places the container prepared for the patient on the top of the cart. Images of the label on the container, e.g. syringe, IV bag, cup containing pills, are taken with the camera and analyzed to verify that the patient receives the medication prescribed for him/her by the physician. The camera can continue to take images of the administration process to provide documentation that the medication has been properly administered.

In working with syringes one common problem is the presence of air bubbles together with the liquid that is drawn into the barrel of the syringe. Air bubbles affect the accuracy of the dosage and, if injected into a blood vessel of the patient, can cause serious and sometimes fatal complications. Because of the difference in the optical properties there is a visually notable difference between air and the liquid in the syringe. The image processing algorithms are able to identify this difference and thus the presence of bubbles in the images of the filled syringe and to generate a warning to the producer or administrator of the medication (see steps 305, 309, and 315 in FIGS. 4A and 4B). One method of identifying the presence of the bubbles that has been employed in embodiments of the system of the invention—both in the pharmacy and in portable units—is to incline at least a portion of the work surface at an angle, e.g. 5-90 degrees with a horizontal plane. After being tilled with liquid, the syringe is placed on this surface tip up with its longitudinal axis aligned with the slope of the surface. In this configuration the bubble (or bubbles) rises to the top of the liquid and the image processing algorithm can easily identify the bubble and/or measure its actual volume. The algorithm, simultaneously, measures the volume of the liquid drawn to the syringe barrel by 'counting' the marks printed on the wall of the syringe by the manufacturer or by measuring the distance between the syringe piston and the end of its barrel, and calculating the volume by multiplying this distance with the barrels inner diameter, taken from the system's database. Then the algorithm will approve the volume or warn for bubble existence and calculate the actual liquid volume by subtracting the bubble volume from the liquid volume. An alternate method of assisting the software of the system to identify the presence of bubbles in the syringe would be to place the syringe on an illuminated surface or on a transparent surface and to provide a source of illumination under the surface. In this embodiment the incident angle of the light with respect to the syringe might be less than the critical angle of the liquid in the syringe and the light might be polarized to cause optical effects that increase the visibility of the bubbles. In another embodiment the syringe can be held at an angle with the horizontal and the volume of the bubble and/or the liquid in the syringe can be determined from the camera images.

Embodiments of the system of the invention comprise a label printer, which is connected to the system by a wire or wireless communication connection. The label printer finalizes the preparation process for a specific patient. After the preparation process is finished (step 319 in FIG. 4B) a label is printed from the label printer and attached to the IV bag or syringe (IV push), or other container that contains the medicine, which is to be administered to the patient. The labels are clearly marked with information that signifies that the medicine is ready for administration to the patient, e.g. the word "DONE" or "READY" and can be printed with information that can include, for example, the time stamp of preparation and administration; names of the producer; a logo for the system and/or a code that can be matched to the data about the specific preparation, as stored in the system's database. Instead of a printed label an electronic label, e.g. a RFID chip, can be produced and attached to the IV bag or syringe.

Embodiments of the system of the invention may also include other components, for example a UV, ozone, alcohol, or chloroform sterilization unit. The algorithm of the software in the processor of the system are adapted to prompt the user regarding which items involved in the preparation process require sterilization in this unit, at what stage in the preparation process the items should be placed in the unit, and to control the operation of the unit to achieve optimal results.

Although embodiments of the invention have been described by way of illustration, it will be understood that the invention may be carried out with many variations, modifications, and adaptations, without exceeding the scope of the claims.

The invention claimed is:

1. A method for monitoring, documenting and assisting with the manual preparation and/or administration of liquid medications or medications requiring reconstitution, said method comprising:
   a) using at least one digital camera and providing constant surveillance of the preparation/administration process;
   b) using the image acquired by said digital camera to determine whether bubbles are present in the liquid in a syringe and to identify the volume of liquid in said syringe by image processing the relative position of the syringe piston to syringe barrel;
   (c) providing software adapted to perform image processing of images acquired by said at least one digital camera and to compare, in real time, data extracted from the processed images to information relative to one or more of a patient, drug components and composition of said medication, and non-drug items needed in the preparation, wherein said data is automatically or manually retrieved from various sources; and
   (d) providing dedicated software algorithms that are adapted to act as an interactive assistant guiding and/or supervising a producer through each step of a specific preparation process.

2. The method of claim 1, comprising providing software adapted to compile complete documentation of the medication preparation process in the form of visual and data archives of the preparation steps, in which every step in the preparation process is documented and indexed.

3. The method of claim 1, comprising a stage comprised of general steps that are followed for filling any type of prescription; wherein the algorithms in the software are adapted to verify the correct match of a prescription to a patient and to his/her medical condition and to supervise or guide a producer when selecting the prescribed drugs and equipment needed for the preparation process.

4. The method of claim 1, wherein a visual or aural warning alerts the producer, if an error is detected at any stage of the preparation or administration process.

5. The method of claim 3, wherein the images and data that are processed by the software are saved together with the parameters of the objects visible in said images that the software has deduced for them.

6. The method of claim 1, wherein barcode recognition, QR code recognition, OCR (Optical Character Recognition), and additional pattern recognition algorithms are used to supply data from the images.

7. The method of claim 1, wherein images of a syringe are analyzed to determine at least one of the following:
   a) the type and size of said syringe;
   b) whether said syringe is filled with air or transparent liquid;
   c) whether bubbles are present in the liquid in said syringe;
   d) to determine the volume of said bubbles; and
   e) to measure the volume of liquid in said syringe by recognizing the piston of said syringe and a reference line on the barrel of said syringe and measuring the distance between them.

8. A system for monitoring, documenting and assisting with the manual preparation and/or administration of medications, said system comprising:
   a) using at least one digital camera and providing constant surveillance of the preparation/administration process;
   b) a processor unit comprising:
      i) software adapted to perform image processing of images acquired by said at least one digital camera and to compare, in real time, data extracted from the processed images to information relative to one or more of a patient, drug components and composition of said medication, and non-drug items needed in the preparation, wherein said data is automatically or manually retrieved from various sources;
      ii) dedicated software algorithms that are adapted to act as an interactive assistant guiding and/or supervising a producer through each step of a specific preparation process; and
   c) a display screen adapted to serve as an interface between said producer and the software of said system.

9. The system of claim 8, wherein the processor unit additionally comprises software adapted to compile complete documentation of the medication preparation process in the form of visual and data archives of the preparation steps, in which every step in the preparation process is documented and indexed.

10. The system of claim 8, adapted to produce a visual or aural warning to alert the producer if an error is detected at any stage of the preparation or administration process.

11. The system of claim 8, wherein the image processing software is adapted to use barcode recognition, QR code recognition, OCR (Optical Character Recognition), and additional pattern recognition algorithms to supply data from the images.

12. The system of claim 8, wherein the image processing software is adapted to process images of a syringe taken by the at least one digital camera in order to determine at least one of the following:
   a) the type and size of said syringe;
   b) whether said syringe is filled with air or transparent liquid;
   c) whether bubbles are present in the liquid in said syringe;
   d) to determine the volume of said bubbles; and
   e) to measure the volume of liquid in said syringe by recognizing the piston of said syringe and a reference line on the barrel of said syringe and measuring the distance between them.

13. The system of claim 12, comprising an illuminated surface on which a syringe can be placed.

14. The system of claim 13, wherein the source of illumination is polarized to cause optical effects that increase the visibility of the bubbles.

15. The system of claim 8, wherein said system is adapted to be portable.

* * * * *